United States Patent
Sharon et al.

[11] Patent Number: 6,089,233
[45] Date of Patent: Jul. 18, 2000

[54] DIVING MASK SUPPLEMENTED WITH A DEVICE FOR EQUALIZING PRESSURE ACROSS THE EARDRUM OF DIVERS

[75] Inventors: Arieh Sharon, Ramat Gan; Howard Rosenstein, Hofit, both of Israel

[73] Assignee: Safe Dive Ltd., Ramat Gan, Israel

[21] Appl. No.: 09/161,657

[22] Filed: Sep. 29, 1998

[51] Int. Cl.$^7$ .................................................. A61F 11/00
[52] U.S. Cl. ............................................ 128/864; 28/866
[58] Field of Search .................................. 128/845, 846, 128/864–867, 206.26, 207.4, 201.29; 2/2.14, 2, 428

[56] References Cited

U.S. PATENT DOCUMENTS

| | | |
|---|---|---|
| 1,324,747 | 12/1919 | Runyan ............................. 128/207.11 |
| 2,362,917 | 11/1944 | Malcom . |
| 2,488,235 | 11/1949 | Pfeiffer ....................................... 2/428 |
| 3,102,538 | 9/1963 | Cowan . |
| 3,110,356 | 11/1963 | Mendelson . |
| 3,415,246 | 12/1968 | Hill . |
| 3,787,899 | 1/1974 | Krawagna . |
| 3,944,018 | 3/1976 | Satory . |
| 4,219,018 | 8/1980 | Draper, Jr. . |
| 4,253,452 | 3/1981 | Powers et al. . |
| 4,384,575 | 5/1983 | Asker . |
| 4,406,282 | 9/1983 | Parker et al. . |
| 4,724,922 | 2/1988 | Kalayjian . |
| 4,774,938 | 10/1988 | Leight . |
| 4,896,380 | 1/1990 | Kamitani . |
| 4,896,679 | 1/1990 | St. Pierre . |
| 4,913,165 | 4/1990 | Fishgoyt . |
| 5,483,975 | 1/1996 | Hirschenbain .......................... 128/864 |
| 5,603,125 | 2/1997 | Chou . |
| 5,713,078 | 2/1998 | DeAngelis . |

*Primary Examiner*—Michael A. Brown
*Attorney, Agent, or Firm*—Mark M. Friedman

[57] ABSTRACT

A diving mask supplemented with a device for facilitating the equalization of pressure across the eardrum of a user, including (a) a mask body configured to closely fit the face of the user so as to cover at least the eyes and nose of the user, so that, when in use, the mask body and the face of the user define a first closed space, the mask body including a transparent window through which the user sees; (b) first and second ear cups for closely covering the ears of the user, the ear cups and the sides of the head of the user define a second and third closed spaces around the ears of the user, respectively, each of the ear cups including (i) a flexible ear cover for covering an ear of the user; (ii) an external solid frame for supporting the ear cover; and (iii) a solid outer cover for protecting the ear cover; (c) first and second tubes extending from the mask body, each of the first and second tubes having a first end and a second end, the first ends communicating with the first closed space defined by the mask body and the face of the user, the second ends communicating with the second and third closed spaces, respectively, defined by the ear cups and the sides of the head of the user; and (d) a strap arrangement connecting between each of the first and second ear cups and the mask body and between the first and second ear cups.

20 Claims, 6 Drawing Sheets

DIVING MASK SUPPLEMENTED WITH A DEVICE FOR EQUALIZING PRESSURE ACROSS THE EARDRUM OF DIVERS

FIELD AND BACKGROUND OF THE INVENTION

The present invention relates to underwater diving equipment and, more particularly, to diving mask including a devices for facilitating the equalization of pressure between the diver's middle and outer ear.

Figure 1:
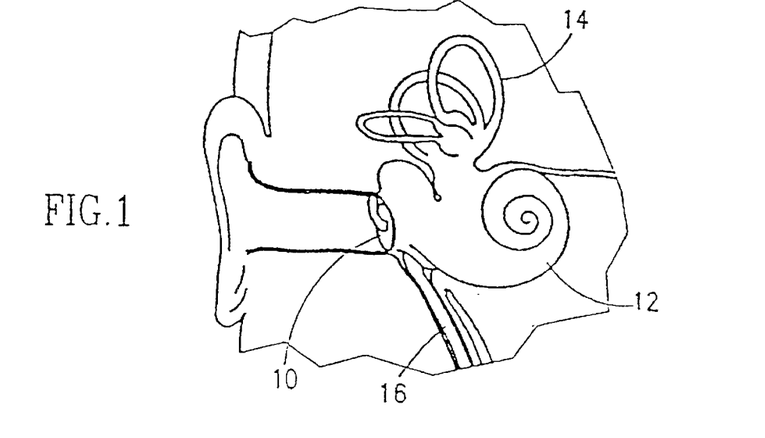
FIG. 1 is a cross-sectional view of the human ear.

As shown in FIG. 1, the human ear is made up of three sections, commonly designated the outer ear, the middle ear and the inner ear. The outer ear includes the portion of the ear from the eardrum 10 outward to the ear opening. The inner ear includes the cochlea 12 and the three semicircular canals 14. The middle ear is that portion of the ear between the eardrum 10 and the inner ear.

Figure 2:
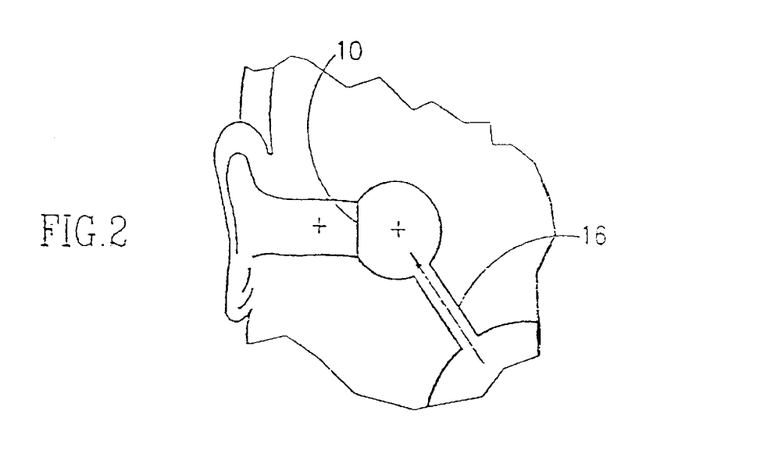
FIG. 2 is a schematic view of the human ear under pressure equalization.

The middle ear is connected to the mouth cavity (not shown) through the eustachian tube 16, whose chief function is to equalize the pressure between the middle ear and the mouth cavity (typically the ambient pressure). Thus, under normal conditions, whenever the ambient pressure rises, the pressure in the outer ear rises, as does the pressure in the mouth cavity. The rise in pressure in the mouth cavity brings about a concomitant rise in the middle ear through the eustachian tubes. The result is adequate pressure equalization between the outer and middle ear across the eardrum (see FIG. 2).

The pressure equalization is particularly important for divers since the ambient pressure changes dramatically and rapidly as the diver lowers himself beneath the water surface or rises toward the water surface.

Figure 3:
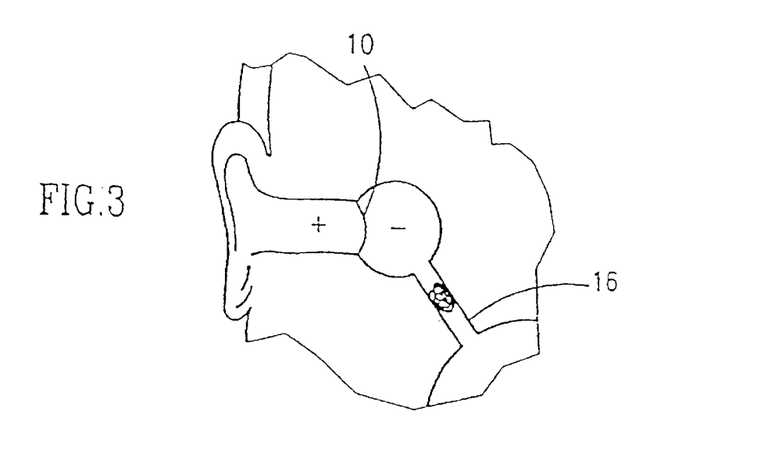
FIG. 3 is a schematic view of the human ear with a blocked eustachian tube which prevents pressure equalization.

The pressure equalization may be delayed or prevented when secretions block the eustachian tubes (see FIG. 3). This may be the case when the diver's eardrum is excited by low temperatures, water or pressure which brings about edema with its excessive secretion from the mucous membranes surrounding the middle ear and the eustachian tube. The edema further narrows the eustachian tubes.

Furthermore, when diving the pressure on the outer ear increases almost instantaneously while the pressure in the middle ear increases at a lower rate, because of the narrowness of the eustachian tubes, which causes, for a short time, a relative under-pressurized condition in the middle ear. This under-pressure can stimulate the secretion of mucous and blood from the tissue surrounding the middle ear and eustachian tube and could lead to the blockage of the eustachian and the prevention of further pressure stabilization.

The result of a pressure differential between the outer and middle ear can vary from discomfort to great pain and could, in some cases, lead to the rupture of the eardrum.

Additionally, it is desirable to prevent the entry of cold, saline or polluted water into the ear, which could result in loss of balance, stimulated ear mucous and blood secretions and bacterial infections.

To prevent the pressure equalization and related difficulties, it has been proposed to prevent entrance of water into the ear and to provide external tubes which functionally supplement the eustachian tubes and which serve to equalize the pressure across the eardrum.

U.S. Pat. No. 4,896,380 discloses a facemask which is equipped with a pair of tubes. Each tube features an earplug at its far end. Each of the earplugs can be plugged into the ear canal and air from the facemask is able to reach the outer ear through the tube in order to equalize the pressure across the eardrum. A disadvantage of such a system is that the air pressure from the mask is transferred directly to the outer ear without any delay or attenuation which could cause the user considerable discomfort. In addition, the earplugs tend to get dislodged from the ears during a dive, which leads to a radical change in local temperature creating a considerable discomfort and may lead to barotrauma. A further disadvantage is that upon dislodging of one of the tubes would create a significant pressure difference in the two ears which could greatly inconvenience the diver.

U.S. Pat. No. 2,488,235 also discloses an underwater facemask equipped with a pair of tubes. Each tube communicates at its far end with a substantially semi-spherical ear cup which covers the user's ear. The strap of the facemask serves to push the ear cups toward the user's ears. A disadvantage of such a system is that the strap securing the facemask to the face of the diver and the ear cups are essentially separate units so that the strap exerts inward pressure on the ear cups without relation to the ambient water pressure which destroys any chance of fine tuning the pressure on the user's ears, as described below. Furthermore, U.S. Pat. No. 2,488,235 fails to disclose a mechanism for adjusting the position of the ear cups to a specific user.

U.S. Pat. No. 5,483,975 teaches a device for facilitating the equalization of pressure across the eardrum of a user which typically includes a facemask configured to fit over at least the eyes and nose of the user. The device further includes a strap for securing the facemask to the face of the user. The strap, when secured to the head of the user, defines a single air space which includes ear portions overlying the user's ears and a connecting portion overlying the sides and back of the user's head and connecting the ear portions. Finally, the device includes a tube for supplying air to the air space. One end of the tube is connected to the air space while the other end of the tube is connected to a source of pressurized air, such as the facemask, the air supply controller or the air supply mouthpiece. A disadvantage of such a device is that the strap is traditionally used for tightly securing the mask to the user's face, such that it becomes water impermeable. Such a device requires also adjustments of the ear portions, such that they fit the position of the ears of a specific user. As further detailed below, a mechanism for adjusting the position of the ear portions and for further tightly securing the mask to the users face requires both front and rear adjustments. However, due to the function of the strap as a single air space providing a rear adjustment is not feasible.

There is thus a widely recognized need for, and it would be highly advantageous to have, a simple and reliable device connectable to a diving mask which will aid divers by equalizing the pressure between the outer and middle ear and between the two ears of the diver in a way which will minimize or eliminate discomfort.

SUMMARY OF THE INVENTION

According to one aspect of the present invention there is provided a diving mask supplemented with a device for facilitating the equalization of pressure across the eardrum of a user, comprising (a) a mask body configured to closely fit the face of the user so as to cover at least the eyes and nose of the user, so that, when in use, the mask body and the face of the user define a first closed space, the mask body including a transparent window through which the user sees; (b) first and second ear cups for closely covering the ears of the user, the ear cups and the sides of the head of the user define a second and third closed spaces around the ears of the user, respectively, each of the ear cups including (i) a flexible ear cover for covering an ear of the user; (ii) an external solid frame for supporting the ear cover; and optionally (iii) a solid outer cover for protecting the ear cover; (c) first and second tubes extending from the mask body, each of the first and second tubes having a first end and a second end, the first ends communicating with the first closed space defined by the mask body and the face of the user, the second ends communicating with the second and third closed spaces, respectively, defined by the ear cups and the sides of the head of the user; and (d) a strap arrangement connecting between each of the first and second ear cups and the mask body and between the first and second ear cups.

According to another aspect of the present invention there is provided an ear cup for underwater use comprising (a) a flexible ear cover for covering an ear of a user, the flexible ear cover designed for defining a closed space with an ear of the user and for accepting a tube for pressure equilibration within the closed space; (b) an external solid frame for supporting the ear cover and for translatably accepting a strap for supporting the ear cup when used, the ear cover being snappable to the external solid frame; and optionally (c) a solid outer cover for protecting the ear cover, the solid outer cover being snappable to the external solid frame.

According to yet another aspect of the present invention there is provided a diving mask supplemented with a device for facilitating the equalization of pressure across the eardrum of a user, comprising (a) a mask body configured to closely fit the face of the user so as to cover at least the eyes and nose of the user, so that, when in use, the mask body and the face of the user define a first closed space, the mask body including a transparent window through which the user sees; (b) first and second ear cups for closely covering the ears of the user, the ear cups and the sides of the head of the user define a second and third closed spaces around the ears of the user, respectively; (c) first and second tubes extending from the mask body, each of the first and second tubes having a first end and a second end, the first ends communicating with the first closed space defined by the mask body and the face of the user, the second ends communicating with the second and third closed spaces, respectively, defined by the ear cups and the sides of the head of the user; (d) a strap arrangement connecting between each of the first and second ear cups and the mask body and between the first and second ear cups; and (e) first and second unidirectional valves present between the mask body and each of the first and second tubes, for effecting flow from the first closed space into the tubes, yet restricting a reverse flow, such that if any of the first and second tubes disconnects underwater, water is prevented from entering the first closed space.

According to still further features in the described preferred embodiments the external solid frame is formed with a strap accepting mechanism, such that each of the ear cups is translatable along the strap arrangement.

According to still further features in the described preferred embodiments the mask body is large enough to cover also the mouth of the user.

According to still further features in the described preferred embodiments the diving mask further comprising at least one audio device implemented in one of the ear cups.

According to still further features in the described preferred embodiments each of the tubes includes at least one spiral portion.

According to still further features in the described preferred embodiments each of the tubes includes at least one corrugated (accordion-like) portion.

According to still further features in the described preferred embodiments the diving mask of claim 1, further comprising first and second unidirectional valves implemented at the first and second ear cups and serve for drainage.

The present invention successfully addresses the shortcomings of the presently known configurations by providing a simple and reliable diving mask supplemented with a device for facilitating the equalization of pressure across the user's eardrums which is particularly useful during undersea diving.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a diving device which can be used to equalize pressure across the eardrum.

The principles and operation of a device according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 4–8 show various aspects of the diving mask and the device for facilitating the equalization of pressure across the eardrums of a user according to the present invention.

A mask body 20 is provided, configured to closely fit the face of the user, so as to cover at least the eyes and nose of the user, so that, when in use, mask body 20 and the face of the user define a first closed space. Mask body is typically made of a rubber-like material, such as, but not limited to, rubber or silicon.

Mask body 20 includes a transparent window 22 through which the user sees. Window 20 can be of any transparent material, such as, but not limited to, glass and transparent plastic.

Figure 4:
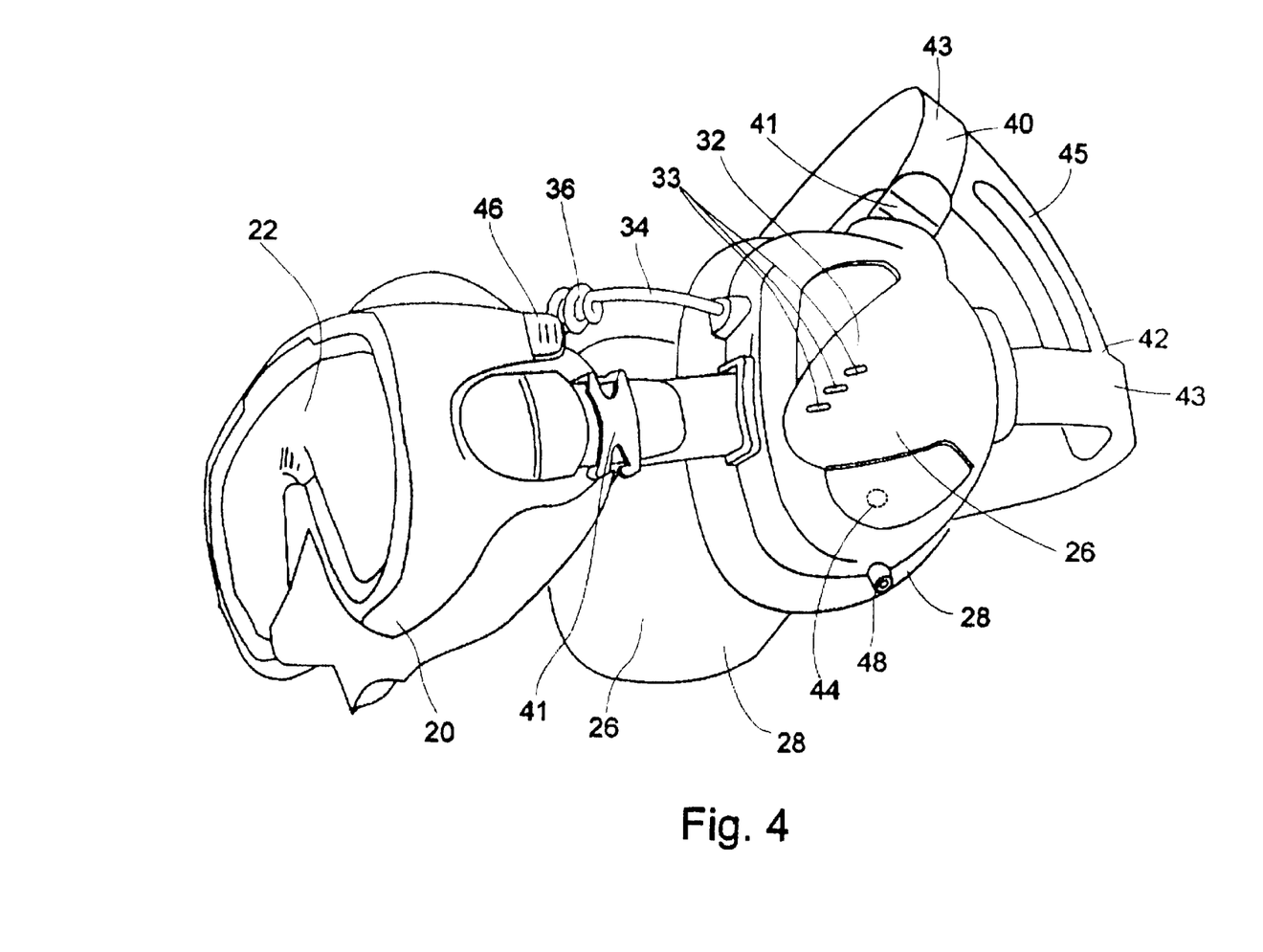
FIGS. 4–8 show several perspective views of a mask supplemented with a device for facilitating the equalization of pressure across the user's eardrums or portions thereof according to the present invention.
Figure 5:
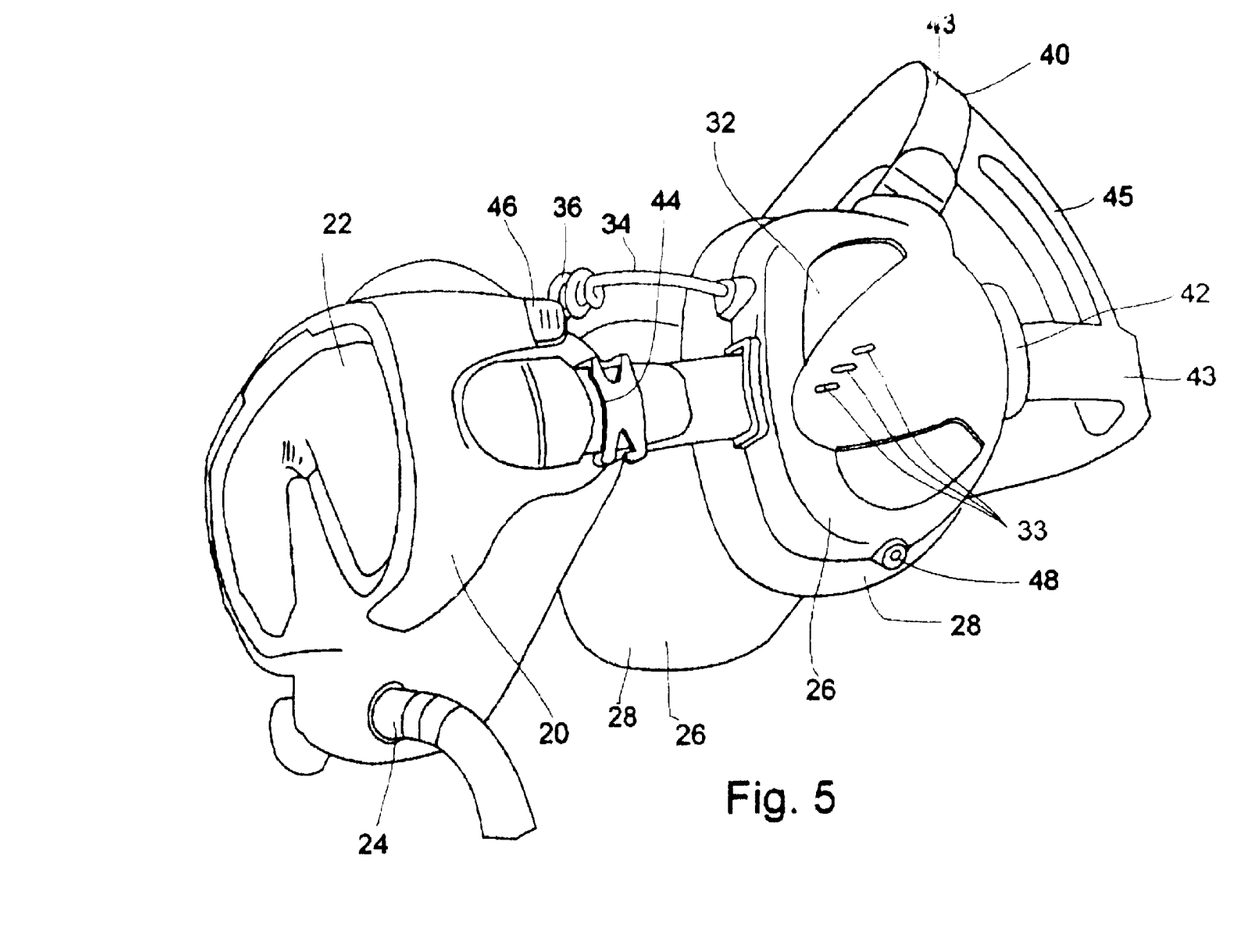
Figure 6:
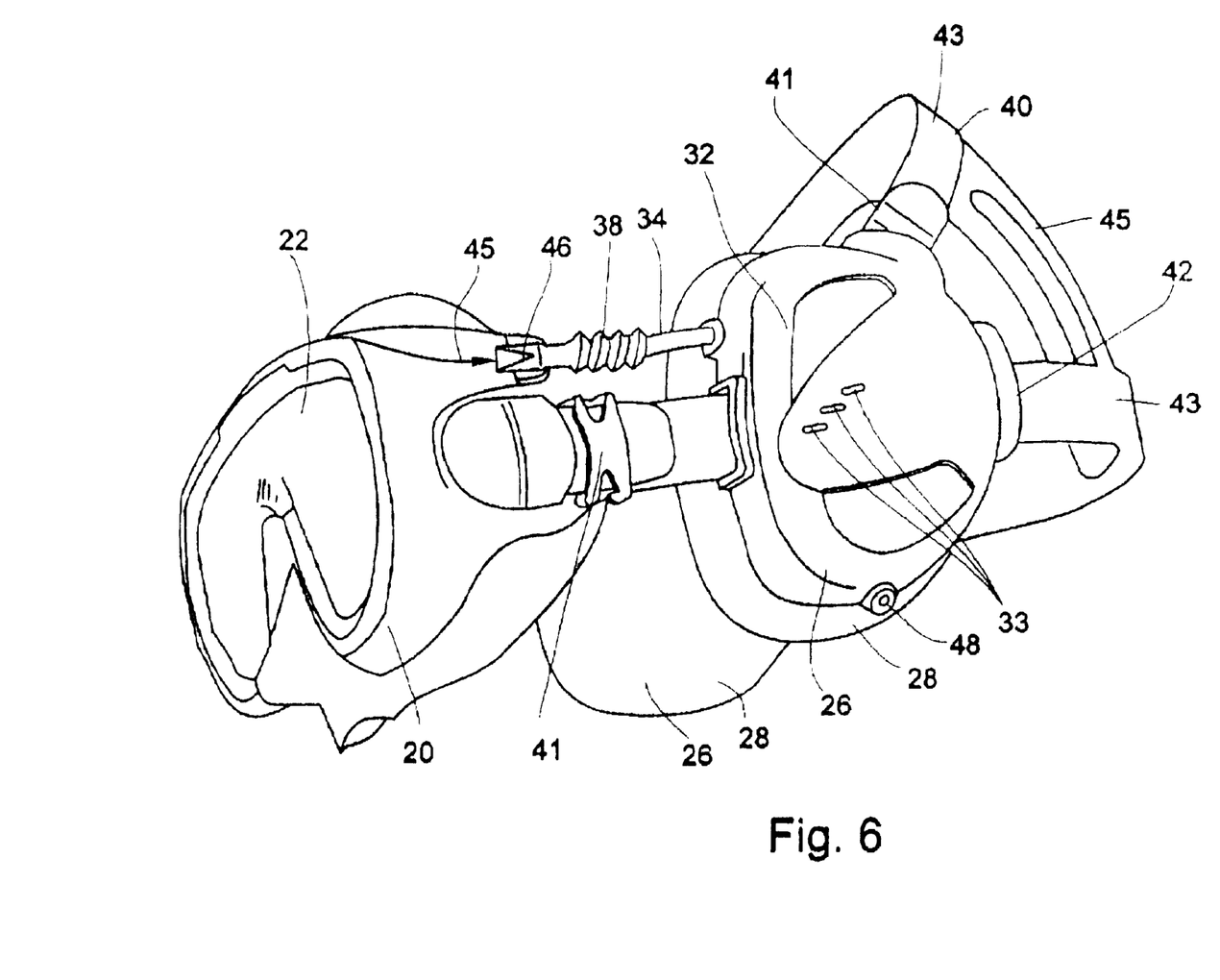
Figure 7:
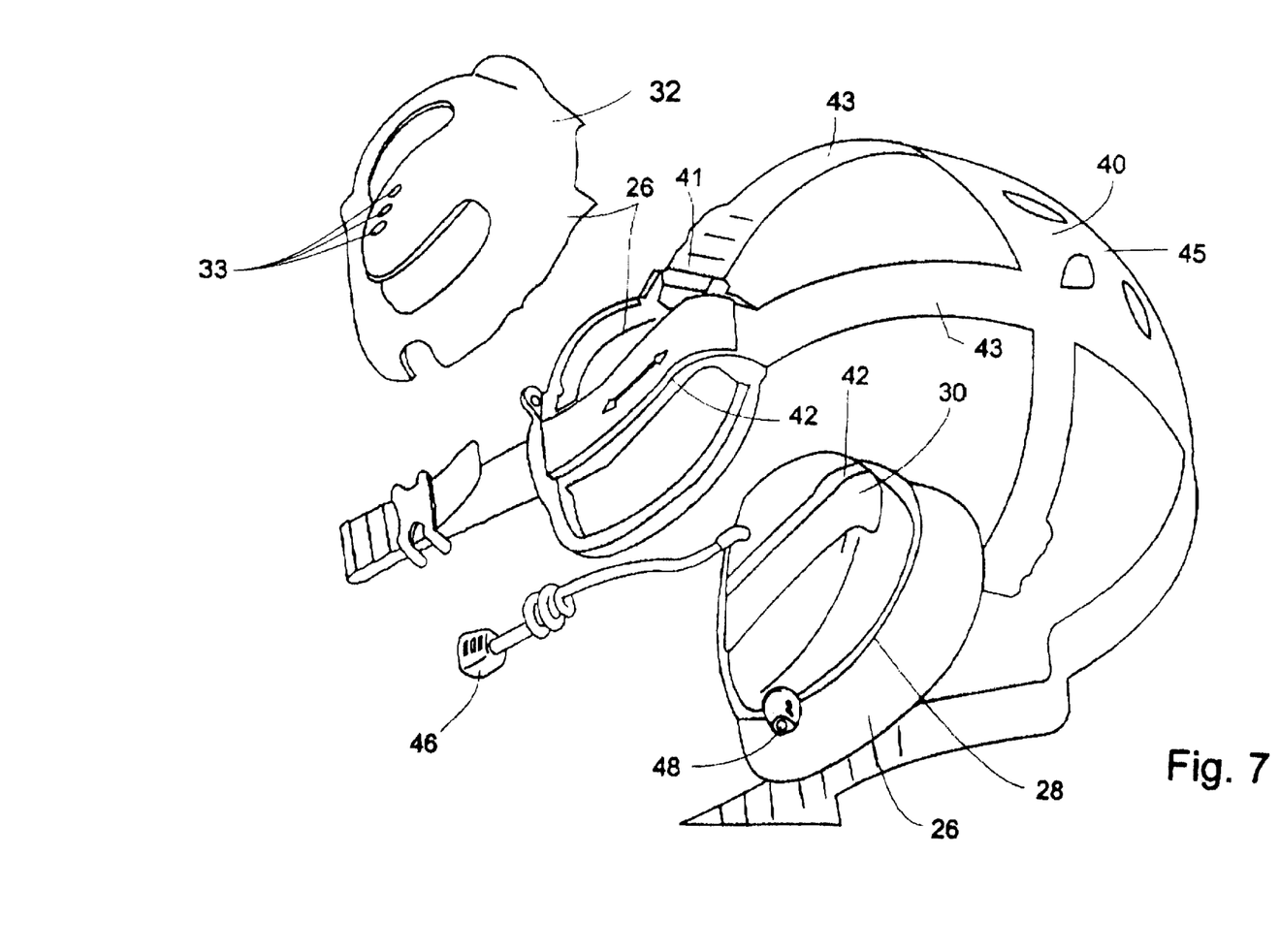
Figure 8:
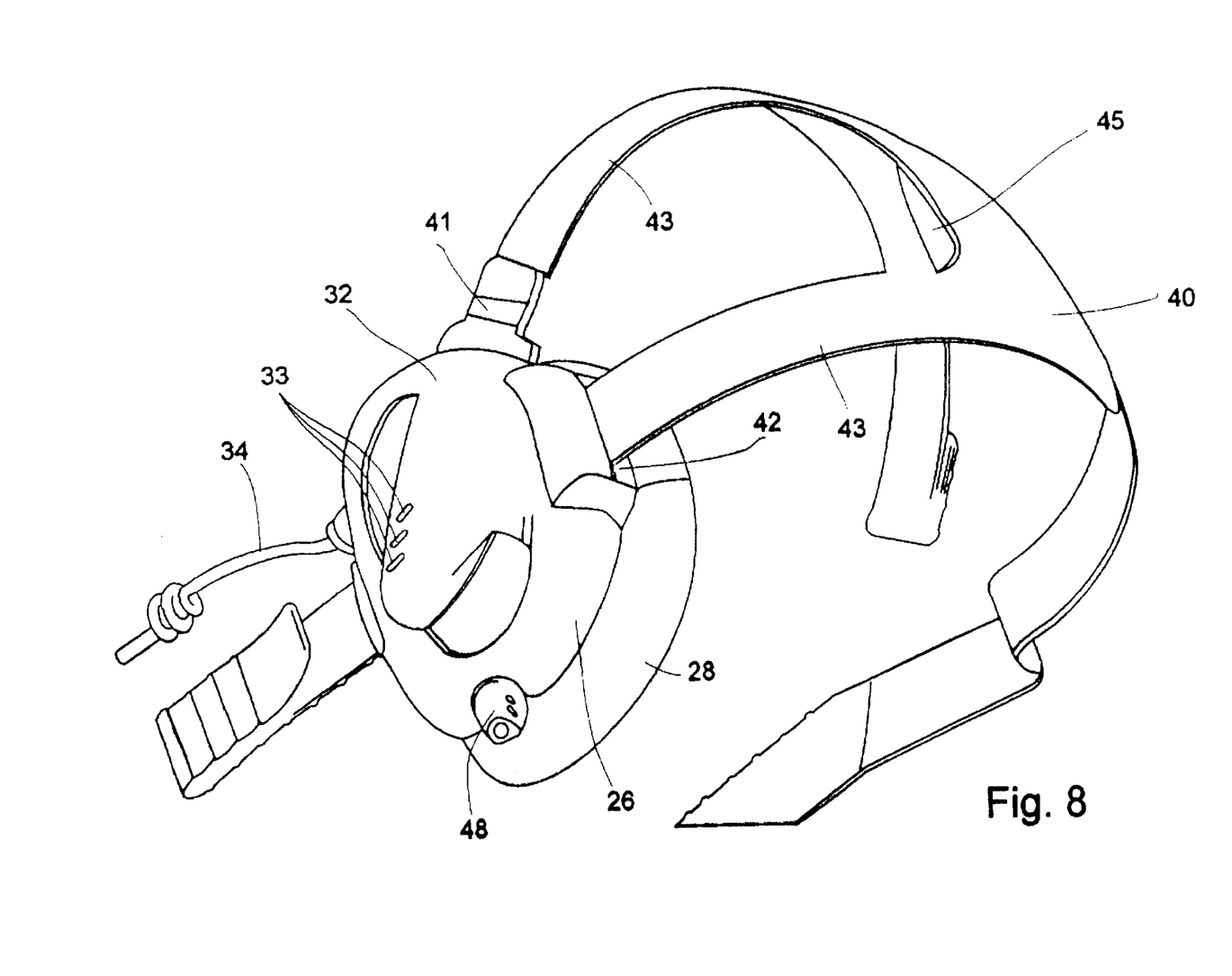

In the configurations shown in FIGS. 4 and 6, mask body 20 is designed to cover the eyes and nose of the user. However, in the configuration of FIG. 5, mask body 20 is designed to cover also the mouth of the user. In the latter case, mask body 20 is further designed to accept a breathing regulator 24 which is connected to the air tanks or other air source used while diving, so as to enable the user to breath underwater.

In any case, mask body 20 is shaped to comfortably accept the nose of the user and to fit the face of the user, such that when tightly secured thereat via a strap arrangement as further detailed hereinunder, water is typically prevented from entering the closed space formed between mask body 20 and the face of the user.

Further provided are first and second ear cups 26. Ear cups 26 serve for closely covering the ears of the user. In fact, when appropriately engaged, ear cups 26 and the sides of the head of the user define second and third closed spaces around the ears of the user, respectively.

Each of ear cups 26 according to the present invention includes a flexible ear cover or a diaphragm 28, made, for example, of silicon, which, as further detailed hereinunder, affects pressure equilibration across the ear drums of the user.

Each of ear covers 28 is snappable into an external solid frame 30, made, for example, of toughened plastic material, which serves for supporting its respective ear cover 28 and for accepting a strap arrangement as further detailed hereinunder.

Each of ear cups 26 optionally further includes a solid outer cover 32, made, for example, of toughened plastic material, for protecting ear covers 28. Each of outer covers 32 is designed snappable with its respective solid frame 30. Outer covers 32 are formed with openings 33 to allow for immediate pressure equilibration thereunderneath and the surrounding water, such that on their outer side ear covers 28 face the ambient pressure at all times. It will be appreciated that frame 28 can also serve as cover 32.

Further provided are first and second tubes (air hoses) 34 extending from mask body 20. Each of first and second tubes 34 has a first end and a second end. The first ends thereof communicate with the first closed space defined by mask body 20 and the face of the user, whereas the second ends thereof communicate with the second and third closed spaces, respectively, defined by ear covers 28 of cups 26 and the sides of the head of the user.

Tubes 34 cause pressure equilibration between the first, second and third closed spaces, such that the pressure in the breathing system and mouth cavity of the user equals the pressure at the outer ear of the user, so as to avoid the harmful pressure non-equilibrium effects described in the Background section above. Tubes 34 can acquire many configurations, two of which are shown in the drawings. For example, as shown in FIGS. 4 and 5, each of tubes 34 can include at least one spiral portion 36, whereas as shown in FIG. 6, each of tubes 34 can include at least one corrugated portion 38, so as to ensure length flexibility.

Further provided is a strap arrangement 40 connecting between each of first and second ear cups 26 and mask body 20 and further between first and second ear cups 26 themselves, so as to enable to engage mask body 20 and ear cups 26 over the head of the user at their appropriate locations as described.

According to a preferred embodiment of the present invention external solid frame 28 is formed with a strap accepting mechanism 42, such that each of ear cups 28 is translatable along strap arrangement 40, so as to enable appropriate positioning thereof with respect to the user's ears. When in place, cover 32 covers mechanism 42 so as to prevent strap arrangement of escaping.

Mechanism 42 also serves to prevent pressure applied to flexible ear covers 28 by strap arrangement 40, so as to limit the pressures cover 28 faces to the ambient pressure from the outside and to the pressure of the breathing system of the user from the inside (which is regulated by the diving regulator to substantially match the ambient pressure at all times, so as to enable effective breathing at different pressures underwater) and to limit distorting forces from hampering the functionality of cover 28.

According to a preferred embodiment of the present invention strap arrangement 40 includes a single piece having two length adjustable straps 43 connected therebetween via rear connecting straps 45, and four fasteners 41, one at each side of mask body 20 and one at each of ear cups 26. This configuration was experimentally found effective in both positioning ear cups 26 and tightly securing them as well as mask body 20 to the head of the user, so as to prevent water leakage to the closed spaces defined thereby.

As shown in FIG. 4, according to a preferred embodiment of the present invention at least one audio device 44 is provided with ear cup 26. Audio device 44 can be used to play music or to provide audio instructions to the user. Device 44 is implemented in one or both ear cups 26. Miniaturized battery operated audio devices are well known devices formed as audio chips which are widely used in computers and answering machines. Such devices are suitable both for repetitive recording of audio data and for playing any recorded data when desired. Positioning device 44 in ear cups 26 ensures that an air medium resides between device 44 and the ear of the user, such that high quality sound is readily achieved.

According to a preferred embodiment of the present invention first and second unidirectional (one-way, non return) valves 46 are present between mask body 20 and each of first and second tubes 34. Valves 46 serve for effecting flow of air from the first closed space into tubes 34, yet for restricting a reverse flow, such that if any of first and/or second tubes 34 disconnects or breaks underwater, water is prevented from entering the first closed space. Unidirectional (one-way, non return) valves are well known in the art and therefore are not further described herein. A cross sectional view of such a valve is shown in FIG. 6. Arrow 45 indicated the flow direction permitted by the valve.

According to a preferred embodiment of the present invention additional unidirectional (one-way, non return) valves 48 are present at first and second ear cups for drainage of water, should water enter the second and third spaces, respectively. Drainage is effected by holding mask body tight and breathing out through the nose, such that air reaching the first and second spaces pushes out water present therein via valves 48.

According to another aspect of the present invention there is provided an ear cup for underwater use, which includes a flexible ear cover 28 for covering an ear of a user, designed for defining a closed space with an ear of the user and for accepting a tube 34 for pressure equilibration within the closed space. The ear cup further includes an external solid frame 30 for supporting ear cover 28 and for translatably accepting a strap 40 for supporting the ear cup when used. Ear cover 26 is snappable to external solid frame 28. The ear cup further includes a solid outer cover 32 for protecting ear cover 28. Solid outer cover 32 is externally snappable to external solid frame 30. The ear cup as described with a tube connected thereto can be used as a retrofit to supplement a conventional (existing) diving mask with ear pressure equilibration capabilities. The only adjustment that needs to be made in the existing diving mask is the formation of two holes in the mask body, for accepting the ends of the tubes. Flexible adapters can be provided to facilitate tube connection thereto.

The present invention enjoys several advantages as compared with prior art devices, such as U.S. Pat. No. 2,488,235, for two main reasons:

First, the use of an external frame prevents distortion of the ear cover (diaphragm) by the strap arrangement.

Second, the use of unidirectional valves ensures that even if one of the tubes disconnects or breaks underwater, water is prevented from entering the mask.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A diving mask supplemented with a device for facilitating the equalization of pressure across the eardrum of a user, comprising:

(a) a mask body configured to closely fit the face of the user so as to cover at least the eyes and nose of the user, so that, when in use, said mask body and the face of the user define a first closed space, said mask body including a transparent window through which the user sees;

(b) first and second ear cups for closely covering the ears of the user, said ear cups and the sides of the head of the user define a second and third closed spaces around the ears of the user, respectively, each of said ear cups including:

(i) a flexible ear cover for covering an ear of the user; and (ii) an external solid frame for supporting said ear cover;

(c) first and second tubes extending from said mask body, each of said first and second tubes having a first end and a second end, said first ends communicating with said first closed space defined by said mask body and the face of the user, said second ends communicating with said second and third closed spaces, respectively, defined by said ear cups and the sides of the head of the user; and (d) a strap arrangement connecting between each of said first and second ear cups and said mask body and between said first and second ear cups.

2. The diving mask of claim 1, wherein each of said ear cups further includes:

(iii) a solid outer cover for protecting said ear cover.

3. The diving mask of claim 1, wherein said external solid frame is formed with a strap accepting mechanism, such that each of said ear cups is translatable along said strap arrangement.

4. The diving mask of claim 1, wherein said mask body is large enough to cover also the mouth of the user.

5. The diving mask of claim 1, further comprising at least one audio device implemented in one of said ear cups.

6. The diving mask of claim 1, wherein each of said tubes includes at least one spiral portion.

7. The diving mask of claim 1, wherein each of said tubes includes at least one corrugated portion.

8. The diving mask of claim 1, further comprising first and second unidirectional valves present between said mask body and each of said first and second tubes, for effecting flow from said first closed space into said tubes, yet restricting a reverse flow, such that if any of said first and second tubes disconnects underwater, water is prevented from entering said first closed space.

9. The diving mask of claim 1, further comprising first and second unidirectional valves implemented at said first and second ear cups and serve for drainage.

10. An ear cup for underwater use comprising:

(a) a flexible ear cover for covering an ear of a user, said flexible ear cover designed for defining a closed space with an ear of the user and for accepting a tube for pressure equilibration within said closed space;

(b) an external solid frame for supporting said ear cover and for translatably accepting a strap for supporting the ear cup when used, said ear cover being snappable to said external solid frame; and (c) a solid outer cover for protecting said ear cover, said solid outer cover being snappable to said external solid frame.

11. The ear cup of claim 1, further comprising:

(c) a tube connected to said flexible ear cover for pressure equilibration within said closed spaces.

12. A diving mask supplemented with a device for facilitating the equalization of pressure across the eardrum of a user, comprising:

(a) a mask body configured to closely fit the face of the user so as to cover at least the eyes and nose of the user, so that, when in use, said mask body and the face of the user define a first closed space, said mask body including a transparent window through which the user sees;

(b) first and second ear cups for closely covering the ears of the user, said ear cups and the sides of the head of the user define a second and third closed spaces around the ears of the user, respectively;

(c) first and second tubes extending from said mask body, each of said first and second tubes having a first end and a second end, said first ends communicating with said first closed space defined by said mask body and the face of the user, said second ends communicating with said second and third closed spaces, respectively, defined by said ear cups and the sides of the head of the user;

(d) a strap arrangement connecting between each of said first and second ear cups and said mask body and between said first and second ear cups; and (e) first and second unidirectional valves present between said mask body and each of said first and second tubes, for effecting flow from said first closed space into said tubes, yet restricting a reverse flow, such that if any of said first and second tubes disconnects underwater, water is prevented from entering said first closed space.

13. The diving mask of claim 12, wherein said mask body is large enough to cover also the mouth of the user.

14. The diving mask of claim 12, further comprising at least one audio device implemented in one of said ear cups.

15. The diving mask of claim 12, wherein each of said tubes includes at least one spiral portion.

16. The diving mask of claim 12, wherein each of said tubes includes at least one corrugated portion.

17. The diving mask of claim 12, further comprising first and second unidirectional valves implemented at said first and second ear cups and serve for drainage.

18. The diving mask of claim 12, wherein each of said ear cups includes:

(i) a flexible ear cover for covering an ear of the user;

(ii) an external solid frame for supporting said ear cover.

19. The diving mask of claim 18, wherein each of said ear cups further includes:

(iii) a solid outer cover for protecting said ear cover.

20. The diving mask of claim 18, wherein said external solid frame is formed with a strap accepting mechanism, such that each of said ear cups is translatable along said strap arrangement.

\* \* \* \* \*